(12) United States Patent
Young

(10) Patent No.: US 6,219,572 B1
(45) Date of Patent: Apr. 17, 2001

(54) IMAGING USING A CONTRAST AGENT

(75) Inventor: Ian Robert Young, Nr Marlborough (GB)

(73) Assignee: Picker International, Inc., New York, NY (US)

( * ) Notice: Subject to any disclaimer, the term of this patent is extended or adjusted under 35 U.S.C. 154(b) by 0 days.

(21) Appl. No.: 09/296,895

(22) Filed: Apr. 22, 1999

(30) Foreign Application Priority Data

Apr. 25, 1998 (GB) .................................................. 9808761

(51) Int. Cl.[7] ....................................................... A61B 6/00
(52) U.S. Cl. ........................... 600/431; 250/302; 424/9.3; 600/420
(58) Field of Search .................................... 600/420, 431, 600/433, 424, 458; 250/302–304; 424/9.3, 9.4, 9.5

(56) References Cited

U.S. PATENT DOCUMENTS

| 5,906,579 | * | 5/2000 | Vander Salm et al. ............... 600/424 |
| 6,033,645 | * | 3/2000 | Unger et al. .......................... 424/9.5 |
| 6,061,587 | * | 5/2000 | Kucharczyk et al. ................ 600/411 |

FOREIGN PATENT DOCUMENTS

WO 97/24064  7/1997  (WO).

* cited by examiner

*Primary Examiner*—Teresa Walberg
*Assistant Examiner*—Shawntina T. Fuqua
(74) *Attorney, Agent, or Firm*—Timothy B. Gurin; John J. Fry

(57) ABSTRACT

When imaging a region of a patient using a contrast agent, for example in magnetic resonance imaging apparatus including a superconducting magnet 2, it is usual to take an image before and after injection of a contrast agent from an injector 5 into the patient. The invention provides a second injector 8 which contains a sample of the patient's blood or saline or other injectable medium which leads directly to the region of interest being imaged in the patient via a catheter 9, which has an expandible tip which can be expanded to block off the vessel in question. The injector can then be used to inject a bolus of injectable medium into the region of interest, whereupon a further image can be taken, and the catheter can be collapsed to unblock the vein whereupon an image in the presence of the contrast agent can be taken. This enables a second pair of images of the region of interest without and with contrast agent to be prepared, and this can be useful when detecting small blood flows to enable additional sensitivity to be achieved.

13 Claims, 1 Drawing Sheet

IMAGING USING A CONTRAST AGENT

BACKGROUND

Figure 1:
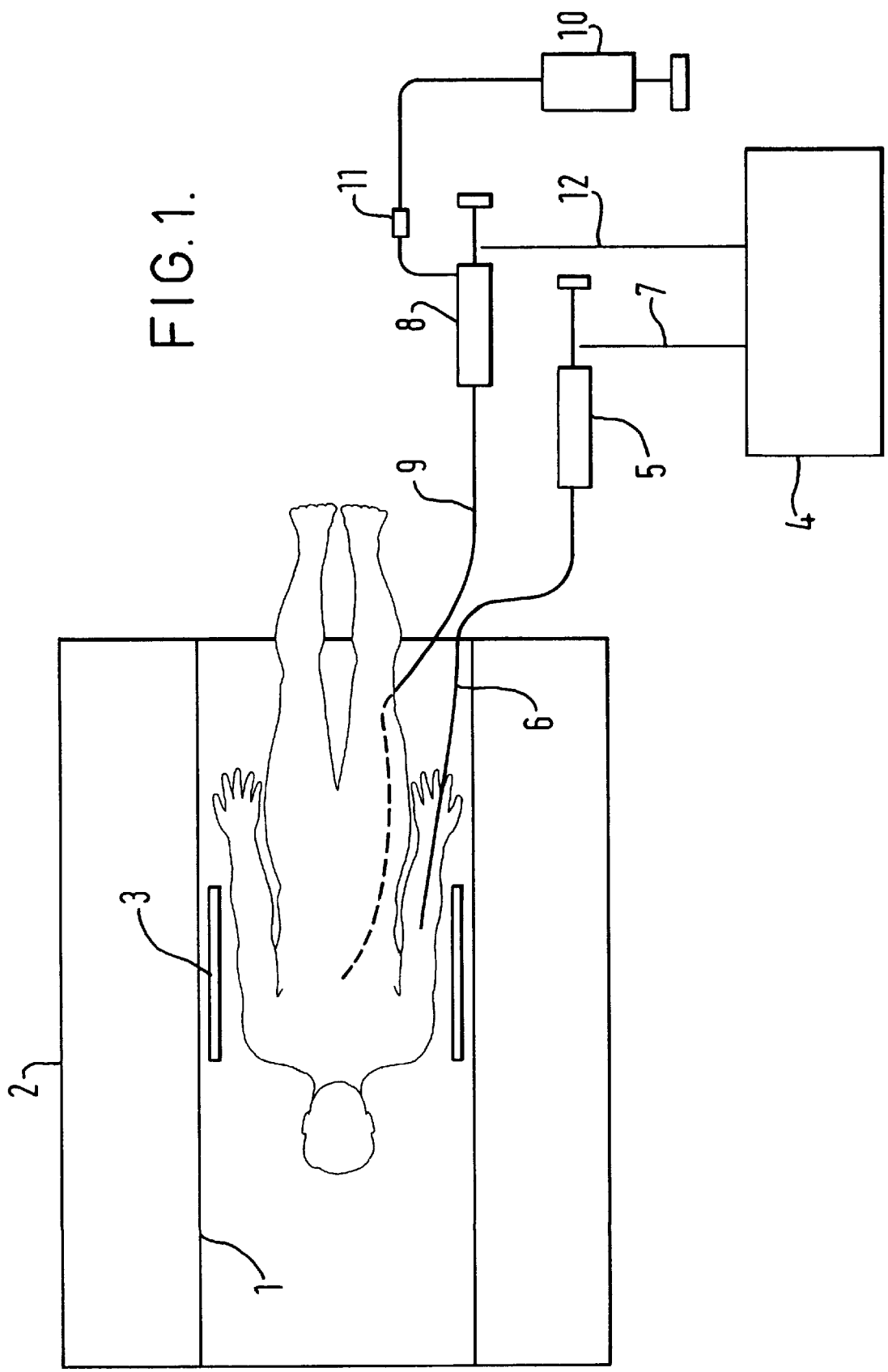

This invention relates to imaging a region of a patient using a contrast agent.

Most methods of imaging can make use of a contrast agent of one kind or another. Typically, a contrast agent is injected into the vascular system of the patient, and circulates through the body in, say, around half a minute. An image taken of the patient then shows enhanced features relating to the contrast agent.

In the case of an X-ray image, a contrast agent such as iodine absorbs X-rays and injected iodinated compounds can be used to improve contrast in view of this.

In the case of magnetic resonance (MR) imaging, a contrast agent such gadolinium chelate affects the local magnetic field and thus the interaction between the tissue to be imaged (in particular the relaxation times of protons of water molecules) and the main magnetic field. This is because the molecules of the contrast agent, which are tumbling about, are paramagnetic.

A commonly used chelate is diethylenetriaminepentaacetic (DTPA). Another contrast agent is gadolinium (Gd) DOTA. Very small iron oxide particles are also used as a contrast agent in MR imaging.

For ultrasound, air in small bubble-like cells is used as a contrast agent.

It would be usual to take an image of a region of interest of the patient before the contrast agent was injected, and then another image after the contrast agent had circulated through the body. Features of interest could be highlighted by the second image.

In the case of angiography, the two images could be subtracted to image the blood flowing through vessels. This could be used to provide information on the functioning of various organs such as the liver, kidney and brain e.g. to ascertain if the blood brain barrier had sustained any damage from a tumour, which would be indicated by blood flow across that barrier.

The problem with MR and X-ray agents is that they are excreted relatively slowly, typically over periods of hours to a few days. This means that once an agent has been given, it is present throughout any subsequent rapidly repeated examination. Hence, where subtle changes are being studied by detecting the presence and absence of the agent, there is only one opportunity for making the observations. This is a particular drawback when studying perfusion (flow through capillaries delivering blood to tissues), because the amount of blood flowing is very small. The significance in the case of MR imaging is that only a small percentage, less than 5%, of tissue protons are intravascular.

SUMMARY

The invention provides a method of imaging a region of a patient using a contrast agent, which comprises the steps of acquiring image information before and after a contrast agent has been injected into the vascular system of the patient, injecting a liquid free of contrast agent through a catheter directly into the vascular system in the vicinity of the region being imaged, and acquiring image information after the liquid has been injected into the vicinity of the region being imaged and after the liquid has been replaced with blood containing the contrast agent.

The invention also provides apparatus for imaging a region of a patient using a contrast agent, comprising means for acquiring image information before and after a contrast agent has been injected into the vascular system of the patient, means for injecting a liquid free of contrast agent through a catheter directly into the vascular system in the vicinity of the region being imaged, and means for acquiring image information after the liquid has been injected into the vicinity of the region being imaged and after the liquid has been replaced with blood containing the contrast agent.

Following injection of the liquid, data can be obtained showing the status of the tissue in the presence of the liquid, and after a further period of time during which mixing of the injected liquid and the rest of the contents of the vascular system almost entirely eliminates the effect of the liquid, further data can be acquired. Image information obtained before and after the liquid introduction may be combined to achieve improved sensitivity especially in the case of small blood flows such as tissue perfusion, or may be compared if an interventional procedure has been carried out before the liquid is injected.

Advantageously, the step of injection of the liquid through the catheter is repeated to enable further image information with and without contrast agent to be acquired. This can be done as many times as is wished.

The catheter is advantageously provided with an expansible tip in order to block a vessel prior to injection of the liquid.

The liquid may be an injectable medium such as saline, or may be blood e.g. taken from the patient prior to the injection of the contrast agent.

The invention is applicable to any method of imaging in which a contrast agent is injected into the vascular system and is excreted relatively slowly, for example, MR imaging, X-ray imaging, ultrasound imaging, gamma ray (nuclear) imaging using injected radiopharmaceuticals, or optical imaging.

DRAWING

FIG. 1 is a plan view of magnetic resonance imaging apparatus and an injector apparatus, parts of which are shown schematically.

DESCRIPTION

Referring to FIG. 1, a patient is located in the bore 1 of a superconducting magnet 2 which is provided with the usual gradient and r.f. coils 3 which, together with the magnet 2, are responsible for generating magnetic field gradients across the patient and providing an r.f. impulse to excite protons in the patient to resonance. A receiver coil (not shown) detects the signals produced as the protons relax and return to their initial state and various planes of the patient may be imaged. Control means 4 is responsible for controlling pulse sequences, and means not shown is provided for analysing the signals received by the receiving coil and reconstructing them into an image of the relevant section of the patient.

The apparatus in the figure is set up to image a slice which includes the patient's heart.

The control means 4 is operated to employ a pulse sequence to take and process such an image. Then, contrast agent contained in injector 5 is injected into a vein in the arm of the patient through a tube 6. The operation of injecting the contrast agent has the effect of operating machine interrupt schematically shown as 7, which is responsible for automatically producing a pulse sequence after a predetermined length of time, say, one minute, to allow the contrast agent to circulate around the patient's body. Accordingly, a second image is produced which is now enhanced by contrast agent.

In accordance with the invention, an injector 8 is provided which feeds injectable liquid along a tube 9 into a catheter inserted in the region of the patient being imaged, in this case, the heart, which is reached by leading it along a vein from the leg. The liquid 8 may be blood taken from the patient before the contrast agent is injected, or may be saline or another injectable medium. A reservoir 10 of the injectable medium is provided and the contents of the injector may be periodically replenished by opening the valve 11.

The catheter is fitted with an expansible tip e.g. a balloon which is expanded prior to operation of the injector in order to block off the blood vessel. Then, when injector 8 is operated, a bolus of the liquid contained in the injector is injected into the vein, and an image taken after this is done now corresponds to the first image taken in which blood free of contrast agent was in the region being imaged. The production of the MR image is automatically set into operation by machine interrupt indicated by reference numeral 12 operated when injector 8 is used. The tip of the catheter is then allowed to collapse, with the result that blood upstream of the catheter containing contrast agent now flows past the tip of the catheter, and a fourth image taken again shows the region of the patient with blood containing contrast agent.

A third pair of images may be taken by repeating the procedure i.e. producing a further injection via the injector 8 and collapsing the tip of the catheter to obtain a view with contrast agent present. The process can be repeated many times until the contents of the reservoir 10 have been used up. The technique would be particularly useful for studying changes in tissue perfusion, because these are small and the acquired images could be correlated to achieve additional sensitivity. Another advantage would be in the case where interventional studies were being performed and it was desirable to detect blood in flow changes to the tissue on a repetitive basis.

The data acquired can be used in various ways. Thus, the image information for each pair of images could be subtracted from each other, and the resulting differential images could then be combined. Or the image information acquired when no contrast agent was present could be combined, as could the image information when contrast agent was present, and the two could then be combined. A single set of data can be analysed and presented with either approach.

The technique is clearly not limited to injections in the region of the heart, and would be applicable to injections in the brain, in which case the tube would be inserted in a vein in the neck, or to any other region of the body.

The contrast agent may be gadolinium DTPA or gadolinium DOTPA or any other suitable material.

Nor is the invention restricted to MR superconducting magnets or even to MR itself. The technique is also applicable to X-ray imaging, to ultrasound imaging, or to nuclear or optical imaging.

The invention has been described with reference to the preferred embodiments. Obviously, modifications and alterations will occur to others upon reading and understanding the preceding description. It is intended that the invention be construed as including all such modifications an alterations insofar as they come within the scope of the appended claims or the equivalents thereof.

What is claimed is:

1. A method of imaging a region of a patient using a contrast agent comprising:

acquiring image information before a contrast agent has been injected into the vascular system of the patient;

acquiring image information after the contrast agent has been injected into the vascular system of the patient;

injecting a liquid free of contrast agent through a catheter directly into the vascular system in the vicinity of the region being imaged; and acquiring image information after the liquid has replaced blood containing the contrast agent in the vicinity of the region being imaged; and acquiring image information after the liquid has been replaced with blood containing the contrast agent.

2. The method of claim 1 further including repeating the steps of injecting the liquid, acquiring image information after the liquid has replaced blood containing the contrast agent, and acquiring image information after the liquid has been replaced.

3. The method of claim 2 wherein the catheter includes an expansible portion and further including using the expansible portion to selectively restrict blood flow in the vascular system in the vicinity of the region being imaged.

4. The method of claim 3 further including prior to injecting the liquid, restricting blood flow in the vascular system in the vicinity of region being imaged; and after acquiring image information after the liquid has been injected, permitting blood flow in the vascular system in the vicinity of the region being imaged.

5. The method of claim 1 wherein the liquid is blood or saline material.

6. The method of claim 1 wherein the catheter includes an expansible portion and further including, prior to the step of injecting the liquid, using the expansible portion to restrict blood flow in the vascular system in the vicinity of the region being imaged.

7. The method of claim 1 wherein the image information is magnetic resonance, x-ray, or ultrasound image information.

8. An apparatus for imaging a region of a patient using a contrast agent, the apparatus comprising:

means for acquiring image information before a contrast agent has been injected into the vascular system of the patient;

means for acquiring image information after the contrast agent has been injected into the vascular system of the patient;

means for injecting a liquid free of contrast agent directly into the vascular system in the vicinity of the region being imaged;

means for acquiring image information after the liquid has replaced blood containing the contrast agent in the vicinity of the region being imaged; and means for acquiring image information after the liquid has been replaced with blood containing the contrast agent.

9. The apparatus of claim 8 wherein the injecting means includes an injector and further including a reservoir operatively connected to the injector.

10. The apparatus of claim 9 further including a valve disposed between the injector and the reservoir.

11. The apparatus of claim 8 further including means for selectively restricting blood flow in the vascular system in the vicinity of the region being imaged.

12. The apparatus of claim 11 wherein the means for selectively restricting includes a catheter having an expansible tip.

13. The apparatus of claim 8 wherein the means for acquiring is a magnetic resonance imager.

* * * * *